US009949542B2

(12) United States Patent
Crne et al.

(10) Patent No.: US 9,949,542 B2
(45) Date of Patent: *Apr. 24, 2018

(54) HAIR COLOURATION, METHOD AND KIT THEREOF

(71) Applicant: Noxell Corporation, Hunt Valley, MD (US)

(72) Inventors: Matija Crne, Wiesbaden (DE); Lars Dahne, Hoppegarten (DE); Gabriella Egri, Berlin (DE); Christian Funk, Berlin (DE); Mathias Kurt Herrlein, Kronberg (DE); Klaus Hilbig, Frankfurt (DE); Moritz Klickermann, Berlin (DE); Tatjana Schafer, Butzbach (DE)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/922,535

(22) Filed: Oct. 26, 2015

(65) Prior Publication Data

US 2016/0120284 A1    May 5, 2016

(30) Foreign Application Priority Data

Oct. 29, 2014 (EP) .................................... 14190884

(51) Int. Cl.
| | |
|---|---|
| A61Q 5/06 | (2006.01) |
| A45D 19/00 | (2006.01) |
| A61Q 5/00 | (2006.01) |
| A61K 8/84 | (2006.01) |
| A61K 8/81 | (2006.01) |
| A61K 8/73 | (2006.01) |

(52) U.S. Cl.
CPC ............... *A45D 19/00* (2013.01); *A61K 8/73* (2013.01); *A61K 8/731* (2013.01); *A61K 8/733* (2013.01); *A61K 8/81* (2013.01); *A61K 8/817* (2013.01); *A61K 8/8117* (2013.01); *A61K 8/8147* (2013.01); *A61K 8/84* (2013.01); *A61Q 5/00* (2013.01); *A61Q 5/065* (2013.01); *A45D 2019/0066* (2013.01); *A61K 2800/43* (2013.01); *A61K 2800/5424* (2013.01); *A61K 2800/5426* (2013.01); *A61K 2800/884* (2013.01)

(58) Field of Classification Search
None
See application file for complete search history.

(56) References Cited

U.S. PATENT DOCUMENTS

| 4,182,612 A | 1/1980 | Sokol |
| 4,445,521 A | 5/1984 | Grollier et al. |
| 4,911,731 A | 3/1990 | Loveless |

| 2008/0282481 A1* | 11/2008 | De Boni ................ A61K 8/817 8/405 |
| 2010/0008885 A1 | 1/2010 | Daly et al. |
| 2011/0083284 A1* | 4/2011 | Suddaby ................ A61K 8/19 8/405 |
| 2016/0120285 A1 | 5/2016 | Crne et al. |

FOREIGN PATENT DOCUMENTS

| EP | 1321131 A2 | 6/2003 |
| WO | WO2011113250 | 9/2011 |
| WO | WO2011113675 | 9/2011 |
| WO | WO2011113676 | 9/2011 |
| WO | WO2011113680 | 9/2011 |
| WO | WO2012119810 | 9/2012 |
| WO | WO2012119811 | 9/2012 |
| WO | WO2012119821 | 9/2012 |
| WO | WO2012126987 | 9/2012 |
| WO | WO-2016069865 A1 | 5/2016 |
| WO | WO-2016069877 A1 | 5/2016 |

OTHER PUBLICATIONS

"U.S. Appl. No. 14/922,615, Restriction Requirement dated Sep. 8, 2016", 10 pgs.
"European Application Serial No. 14190884.8, Extended European Search Report dated May 4, 2015", 7 pgs.
"European Application Serial No. 14190884.8, Response filed Nov. 4, 2016 to Extended European Search Report dated May 4, 2015", 8 pgs.
"European Application Serial No. 14190885.5, Extended European Search Report dated May 4, 2015", 8 pgs.
"European Application Serial No. 14190885.5, Response filed Nov. 4, 2016 to Extended European Search Report dated May 4, 2015", 17 pgs.
"International Application Serial No. PCT/US2015/058020, International Search Report dated Dec. 15, 2015", 5 pgs.
"International Application Serial No. PCT/US2015/058020, Written Opinion dated Dec. 15, 2015", 9 pgs.
International Search Report and Written Opinion, PCT/US2015/057997, dated Dec. 15, 2015.
Charles Zviak: "La coloration temporaire ou fugace" In: Science des traitements capillaires, Jan. 1, 1988 (Jan. 1, 1988), Elsevier Masson, Paris, Milan, Barcelone, Mexico, XPO55183159, pp. 241-245, p. 243.
"Chinese Application Serial No. 201580059595.0, Notice of Passing Preliminary Examination dated May 26, 2017", 1 pg.
"International Application Serial No. PCT/US2015/057997, International Preliminary Report on Patentability dated May 11, 2017", 10 pgs.
"International Application Serial No. PCT/US2015/058020, International Preliminary Report on Patentability dated May 11, 2017", 11 pgs.
"U.S. Appl. No. 14/922,615, Response filed Nov. 16, 2017 to Non Final Office Action dated Jun. 16, 2017", 10 pgs.

* cited by examiner

*Primary Examiner* — Jyothsna A Venkat
(74) *Attorney, Agent, or Firm* — Schwegman Lundberg & Woessner, P.A.

(57) ABSTRACT

Method for coloring hair wherein a first composition comprising at least one cationic polymer and a second composition comprising at least one anionic polymer are alternately applied to the hair.

7 Claims, No Drawings

HAIR COLOURATION, METHOD AND KIT THEREOF

FIELD OF THE INVENTION

The invention relates to a method for colouring hair comprising the application of two different compositions which are successively applied to the hair. The first composition comprises at least one cationic polymer and the second composition comprises at least one anionic polymer. The hair colouration which is obtained according the method of the present invention is particularly advantageous particularly in term of washfastness, stability and tailoring of the colour result.

BACKGROUND OF THE INVENTION

Different methods for changing the natural colour of hair are known in the art. These methods involve the use of hair colouring compositions which allow either permanent or temporary change of hair colour. Hair colouring compositions which are used to permanently change the colour of hair, also called oxidative hair colouring compositions, typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may be irritating for the scalp of the user, especially when such a process is repeated regularly and the compositions which are usually used have an undesirable odour. Furthermore, obtaining the desired colour result is not easy since standard oxidative hair colouring compositions are reactive compositions and it is therefore not easy to control the reaction on hair.

Alternatively, methods for temporarily changing the colour of hair have also been developed. These methods usually involve the application of hair colouring compositions comprising direct dyes. Direct dye compositions are usually less aggressive for the hair in that they are non reactive compositions. However, the problem with these compositions is that the hair colouration which is obtained is typically characterized by a weaker washfastness than when the hair is coloured with standard oxidative hair colouring compositions, especially when the hair is washed with standard shampoo compositions. A further problem with direct dyes is that since direct dyes are low molecular weight molecules, they may have the tendency to also colour the scalp of the user.

Therefore, there is still the need for a hair colouring method providing the hair with the desired colour result and colour intensity in an easy manner. There is also the need for a hair colouring method providing a hair coloration which is characterized by a better stability and good washfastness. Furthermore, there is also the need for a hair colouring method involving the use of hair colouring compositions which are less aggressive for the hair and for the scalp. Finally, there is also the need for a hair colouring method using compositions which are less smelly.

SUMMARY OF THE INVENTION

The present invention relates to a method for colouring hair comprising:
a) carrying out the following sequence of steps:
  i) applying a first composition comprising at least one cationic polymer to a first portion of the hair; and
  ii) applying a second composition comprising at least one anionic polymer to a second portion of the hair;
  the first and the second portions of the hair having at least one common area;
and optionally
b) repeating step a) at least once, wherein the common area of each of the repeated steps
  a) has at least one common area with:
    the common area of step a); and
    the common area of each of the other repeated steps a), in case step a) is repeated more than once;
  wherein in step a) and/or in at least one of the repeated steps a), the cationic polymer is a cationic coloured polymer.

The present invention also relates to a hair colouration obtainable by the above method.

Finally, the present invention also relates to a kit for colouring hair comprising a first compartment comprising the first composition as defined hereinbefore and a second compartment comprising the second composition as defined hereinbefore.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All ratios or percentages are weight ratios or weight percentages unless specifically stated otherwise.

By "cationic polymer" it is meant any polymer comprising an overall charge at full protonation which is positive.

By "cationic coloured polymer" it is meant any cationic polymer comprising at least one chromophore and/or at least one fluorophore either in the skeleton or as pendent group.

By "cationic uncoloured polymer" it is meant any cationic polymer which does not comprise any chromophore or fluorophore either in the skeleton or as pendent group.

By "anionic polymer" it is meant any polymer comprising an overall charge at full deprotonation which is negative.

By "anionic coloured polymer" it is meant any anionic polymer comprising at least one chromophore and/or at least one fluorophore either in the skeleton or as pendent group.

By "anionic uncoloured polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

Method for Colouring Hair

The present invention relates to a method for colouring hair comprising the step a) of carrying out the following sequence of steps:
 i) applying a first composition comprising at least one cationic polymer to a first portion of the hair; and
 ii) applying a second composition comprising at least one anionic polymer to a second portion of the hair,
wherein the first and the second portions have at least one common area.

The second composition is applied after the first composition to the hair.

Having at least one common area between the first portion of the hair to which the first composition is applied and the second portion of the hair to which the second composition is applied ensures that at least a portion of the second composition is applied to the same portion of the hair as at least a portion of the first composition.

The method may further comprises the optional step b) of repeating step a) at least once, wherein the common area of each of the repeated steps a) has at least one common area with the common area of step a) and the common area of each of the other repeated steps a), in case step a) is repeated more than once. This ensures that at least a portion of each of the first and second compositions which are applied to the hair in each of the sequences of steps is applied to the same portion of the hair.

Each of the first compositions of step a) and of the repeated steps a) may be the same or different. Each of the second compositions of step a) and of the repeated steps a) may be the same or different.

In step a) and/or in at least one of the repeated steps a), the cationic polymer is a cationic coloured polymer.

In step a) and/or in each of the repeated steps a), the cationic polymer may be a cationic coloured polymer.

In step a) and/or in each of the repeated step a), the first and the second compositions may be applied all over the hair.

In step b), step a) may be repeated at least at least twice, alternatively at least three times. Alternatively, in step b), step a) may be repeated from 1 to 3 times.

The method according to the present invention is particularly advantageous. Indeed, by carrying out this method, it is possible to provide the hair with the desired colour result and colour intensity in an easy manner. The method is unique in that in each of the sequence of steps a second composition comprising at least one anionic polymer is applied to the hair after a first composition comprising at least one cationic polymer has been applied to the hair.

Since the cationic polymers and the anionic polymers which are comprised in respectively the first composition and the second composition are high molecular weight molecules, they usually do not diffuse into the hair or at least only to a limited extent when compared with dyes used in standard oxidative hair colouring methods. They usually form polymeric layers on hair which are placed on top of each other by alternating the deposition of the cationic polymers and the anionic polymers. By performing the sequence of steps of the method according to the present invention more than once it is possible to obtain more than two polymeric layers on hair and therefore to have a better control on the final colour result and colour intensity which is obtained. By increasing the number of layers which are applied to the hair it is possible to obtain hair colorations having increased colour intensity. The user may decide on how many times the sequence of steps should be repeated and therefore have a better control over the colour result which is obtained on hair.

Furthermore, it is particularly advantageous to apply a second composition comprising at least one anionic polymer to hair after having applied a first composition comprising at least one cationic coloured polymer. Indeed, the polymer which is comprised in the second composition is negatively charged and therefore the outer layer of the coated hair has an electrostatic structure which is similar to the one of the outer layer of natural hair. Therefore it is possible to apply standard cationic conditioners to the hair after the hair coloring process.

It is particularly important for the method according to the present invention to have an anionic polymeric layer which is positioned on top of the cationic polymeric layer. Indeed, the presence of the anionic layer is essential in order to have the possibility of applying a subsequent cationic layer on top of it when the sequence of steps of the method is carried out more than once. While not wishing to be bound by theory it is also believed that in some embodiments, the anionic polymeric layer may act as a protective layer for the cationic coloured layer which is placed underneath and therefore may contribute to the good washfastness of the hair coloration.

Furthermore, the compositions which are used in the method according to the present invention are particularly advantageous since contrary to standard oxidative hair colouring compositions, these compositions are typically odourless.

In the embodiments wherein in step b) of the method, step a) is repeated once, the first composition of step a) may comprise at least one cationic coloured polymer and the first composition of the repeated a) may comprise at least one cationic uncoloured polymer.

The method may further comprise step c) of applying after step a) a third composition comprising at least one cationic polymer to a third portion of the hair wherein the third portion of the hair has at least one common area with the common area of step a).

Alternatively, the method may further comprise the step d) of applying after step b) a third composition comprising at least one cationic polymer to a third portion of the hair, wherein the third portion of the hair has at least one common area with the common area of step b).

In the steps c) and/or d), the third composition may be applied all over the hair. The cationic polymer comprised in the third composition may be a cationic coloured polymer or a cationic uncoloured polymer.

By having a cationic polymeric layer on top of the anionic layer it is possible to provide the user with a good hair feeling which is similar to what is obtained when standard commercially available conditioners are applied to the hair.

Steps i) and/or ii) of the sequence of steps of the method may further comprise the subsequent sub-step of removing the excess of respectively the first composition and/or the second composition from the hair.

Steps i) and/or ii) of the sequence of steps of the method may further comprise the subsequent sub-step of applying energy to the hair in the form of heat, ultrasounds, infrared and/or microwaves. This sub-step may be carried out either after the application of the first or second composition to the hair or after removing the excess of the first composition or the second composition from the hair. While not wishing to be bound by theory, it is believed that applying energy to the hair may accelerate the speed of formation of the polymeric layers on the hair and therefore may increase the stability of the layers once they are formed on the hair. The hair may be heated to a temperature ranging from 5° C. to 70° C., alternatively 20° C. to 60° C., alternatively 40° C. to 60° C.

Steps i) and/or ii) of the sequence of steps of the method may further comprise the subsequent sub-step of washing and/or rinsing the hair. The hair may be washed and/or rinsed with a liquid selected from the group consisting of a cosmetically acceptable solvent, a solution comprising a cosmetically acceptable solvent and a cosmetically acceptable salt, a shampoo composition and mixtures thereof. Alternatively, the hair may be washed and/or rinsed with water.

After carrying out the method according to the present invention, a conditioning agent may be applied to the hair. Any of the conditioning agents disclosed hereinafter may be applied to the hair.

The hair may be pretreated prior to step i) of the first sequence of steps to modify the number of positive or negative charges in some portions of the hair or all over the hair. This pretreatment may be done using chemical or physical means such as pH change, oxidation, reduction, bleaching, plasma treatment, ozone treatment, electrowetting, dry or wet ion-treatment.

Depending on the charge of the hair, the cationic and/or the anionic polymers may attach more or less easily to the hair and therefore a different colour result may be obtained on different portions of the hair which are differently charged. This pretreatment may therefore help to tailor the colour result which is obtained on different portions of the hair, e.g. to obtain a different colour result on hair roots vs. hair tips.

Cationic Polymer

The cationic polymer which is comprised in the first composition may be selected from the group consisting of cationic coloured polymers, cationic uncoloured polymers and mixtures thereof.

Each of the cationic polymers which are comprised in each of the first compositions of step a) and of the repeated steps a) may be the same or different.

In step a) and/or in each of the repeated steps a), the cationic polymer may be a cationic coloured polymer.

The cationic polymers according to the present invention may comprise at least one monomer unit comprising at least one amino functional group. The amino functional group may be selected from the group consisting of primary, secondary, tertiary, quaternary amino functional groups and mixtures thereof. Alternatively, the amino functional group may be selected from the group consisting of primary, secondary amino functional groups and mixtures thereof. Alternatively, the amino functional group may be selected from secondary amino functional groups.

The cationic polymers may have a charge density at full protonation of at least 0.3, alternatively at least 0.6, alternatively at least 0.8, alternatively at least 1.0 positive charges per monomer unit.

The cationic polymers may have a weight average molecular weight of more than 0.5 kD, alternatively from 0.5 to 5000 kD, alternatively from 2 to 1000 kD, alternatively from 10 to 500 kD, alternatively from 25 to 70 kD.

The cationic polymers may be selected from the group consisting of linear polyethyleneimine (linear PEI), branched polyethyleneimine (branched PEI), polyallylamine hydrochloride (PAH), polydiallyldimethylammonium chloride (PDADMAC), copolymers thereof and mixtures thereof.

The cationic polymers may be selected from the group consisting of:
a) Linear polyethyleneimine of the formula:

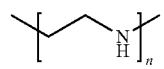

in which n is an integer representing the degree of polymerization, wherein n ranges from 50 to 20,000, alternatively from 100 to 3,500;
b) Branched polyethyleneimine consisting of primary, secondary and tertiary amine groups of the formula:

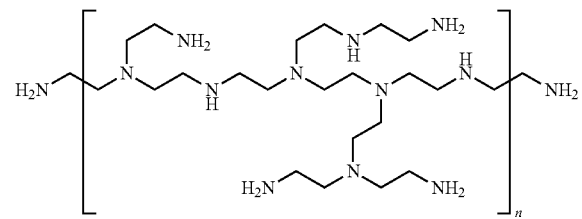

in which n is an integer representing the degree of polymerization, wherein n ranges from 10 to 4,000, alternatively from 50 to 1,000;
c) Polyallylamine hydrochloride (PAH) of the formula:

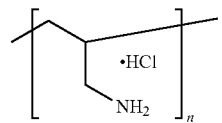

in which n is an integer representing the degree of polymerization, wherein n ranges from 50 to 20,000, alternatively from 150 to 800;
d) Polydiallyldimethylammonium chloride (PDADMAC) of the formula:

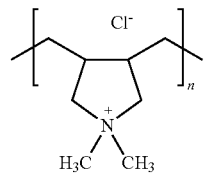

in which n is an integer representing the degree of polymerization,
wherein n ranges from 50 to 20,000, alternatively from 150 to 4,000;
copolymers thereof and mixtures thereof.

The cationic polymers may comprise one or more compounds selected from the group consisting of cosmetically active molecules, care ingredients, optically active molecules, pharmaceutical active molecules, biomarkers and mixtures thereof.

Anionic Polymer

The anionic polymer which is comprised in the second composition may be selected from the group consisting of anionic coloured polymers, anionic uncoloured polymers and mixtures thereof.

Each of the anionic polymers which are comprised in each of the second compositions of step a) and of the repeated steps a) may be the same or different.

In step a) and/or in at least one of the repeated steps a), the anionic polymer may be an anionic coloured polymer.

In step a) and/or in each of the repeated steps a), the anionic polymer may be an anionic coloured polymer.

The anionic polymer may have a charge density at full deprotonation of at least 0.3, alternatively at least 0.6, alternatively at least 0.8, alternatively at least 1.0 negative charges per monomer unit.

The anionic polymer may have a weight average molecular weight of at least 1 kD, alternatively from 10 kD to 1000 kD, alternatively from 70 to 500 kD.

The anionic polymer may comprise at least one monomer unit comprising at least one functional group selected from the group consisting of sulfate, sulfonate, carboxylate, phosphate, phosphonate groups and mixtures thereof. Alternatively, the functional group may be selected from the group consisting of sulfate, sulfonate, carboxylate groups and mixtures thereof.

The anionic polymers may be selected from the group consisting of polystyrene sulfonate (PSS) salts, λ-Carrageenan, dextran sulfate salts, polyacrylic acid (PAA), poly(methacrylic acid) salts, alginic acid salts, carboxymethylcellulose salts, copolymers thereof and mixtures thereof. The salts may be sodium salts.

The anionic polymers may be selected from the group consisting of:

a) Polystyrene sulfonate (PSS) sodium salt of the formula:

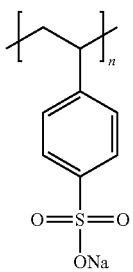

in which n is an integer representing the degree of polymerization, wherein n ranges from 50 to 20,000, alternatively from 150 to 500;

b) Co-polymer of polystyrene sulfonate (PSS) sodium salt and poly(4-styrenesulfonic acid-co-maleic acid) of the formula:

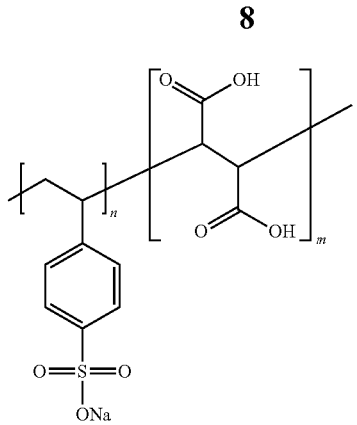

in which n and m are integers representing the degree of polymerization, wherein n+m ranges from 50 to 20,000, alternatively from 150 to 500;

c) λ-Carrageenan;
d) Dextran sulfate sodium salt;
e) Polyacrylic acid (PAA) of the formula:

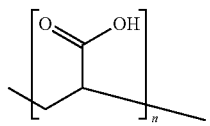

in which n is an integer representing the degree of polymerization, wherein n ranges from 50 to 20,000, alternatively from 150 to 1,000;

f) Alginic acid sodium salt;
g) Carboxymethylcellulose sodium salt of the formula:

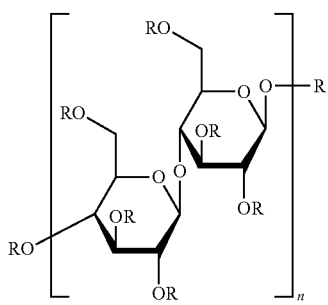

in which:
R is H or $(CH_2)_2COONa$ and
n is an integer representing the degree of polymerization; copolymers thereof and mixtures thereof.

The anionic polymers may comprise one or more compounds selected from the group consisting of cosmetically active molecules, care ingredients, optically active molecules, pharmaceutical active molecules, biomarkers and mixtures thereof.

Cationic Coloured Polymers and Anionic Coloured Polymers

The cationic coloured polymers and the anionic coloured polymers comprise at least one chromophore and/or at least one fluorophore. Any of the hereinbefore exemplified cationic polymers or anionic polymers can comprise at least one chromophore and/or at least one fluorophore either in the skeleton or as pendent group.

The chromophores may be selected from the group consisting of radicals derived from nitrobenzene, azo, imine, hydrazine, phenothiazine, xanthene, phenanthridine, phthalocyanin and triarylmethane-based dyes, and those obtained from direct dyes containing a carbonyl group and mixtures thereof. The chromophores may be selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

The chromophores may be substituted with at least one amine, hydroxyl, sulfate, sulfonate, carboxylate, phosphate, phosphonate, or halide group. These chromophores may be selected from the group consisting of radicals derived from acidic nitro direct dyes, acidic azo dyes, acidic azine dyes, acidic triarylmethane dyes, acidic indoamine dyes and non-quinone acidic natural dyes, and mixtures thereof.

The chromophores may also be selected from derivatives of any of the direct dyes exemplified in the direct dyes section of this application.

The fluorophores may be selected from the group consisting of radicals derived from di-, tetra- or hexa-sulfonated triazine-stilbenes, coumarins, imidazolines, diazoles, triazoles, benzoxazolines, biphenyl-stilbenes optical brighteners, and mixtures thereof.

A cationic coloured polymer or an anionic coloured polymer may comprise the same type of chromophore and/or fluorophore or different types of chromophores and/or fluorophores. Having a cationic coloured polymer or an anionic coloured polymer with different types of chromophores and/or fluorophores may help to cover a broad range of colour shades which can be obtained on hair which are coloured according to the method of the present wherein the first composition or the second composition comprises such a cationic coloured polymer or such an anionic coloured polymer.

The cationic coloured polymers may be selected from the group consisting of:
  i. Coloured linear or branched polyethyleneimine (PEI) of the formula:

in which n and m are integers representing the degree of polymerization, wherein m/n ranges from 0 to 1,000 provided that n is different from 0 and/or m+n ranges from 50 to 20,000, alternatively from 100 to 3,500;
  ii. Coloured polyallylamine hydrochloride of the formula:

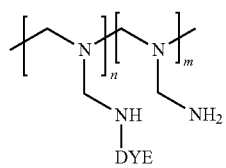

in which n and m are integers representing the degree of polymerization, wherein m/n ranges from 0 to 1,000 provided that n is different from 0 and/or m+n ranges from 50 to 20,000, alternatively from 150 to 800;
  iii. Coloured polydiallyldimethylammonium chloride of the formula:

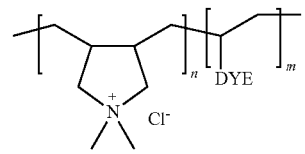

in which n and m are integers representing the degree of polymerization, wherein m/n ranges from 0 to 1,000 provided that n is different from 0 and/or m+n ranges from 50 to 20,000, alternatively from 100 to 3,500;
wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The cationic coloured polymers may be selected from linear polyethyleneimine (PEI)—Rhodamine B of the formula:

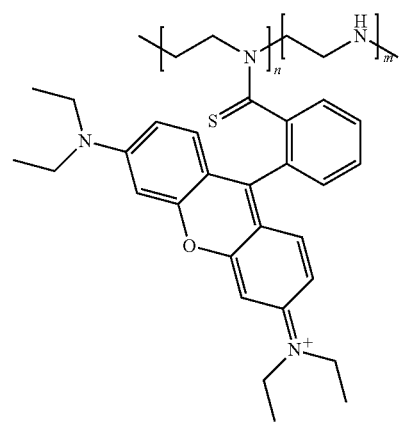

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The anionic coloured polymers may be selected from anionic coloured polymers with the following formula:

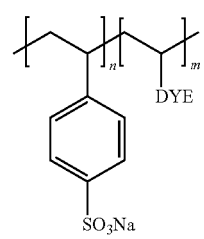

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

Compositions

Solvents

The first and/or the second compositions which are used to carry out the method according the present invention may further comprise a solvent. The solvent may be selected from water, or a mixture of water and at least one organic solvent to dissolve the compounds that would not typically be sufficiently soluble in water. The first and/or the second compositions may be aqueous compositions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the composition may comprise water as a main ingredient, particularly in a total amount ranging from at least 50%, alternatively from at least 60%, alternatively from at least 70%, by total weight of the composition. Typically, when present, the composition comprises a total amount of organic solvents ranging from about 1% to about 30%, by total weight of the composition.

Concentrations

The first composition may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

The second composition may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

pH

The first and/or second composition may have a pH ranging from 2 to 14, alternatively from 3 to 11, alternatively from 5 to 10, alternatively from 7 to 9.

Salt

The first and/or the second composition may comprise a cosmetically acceptable salt at a concentration ranging from 0 to 1.5 mol/L, alternatively from 0.05 to 1 mol/L, alternatively from 0.2 to 0.5 mol/L.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Applicators

The first and/or the second compositions may be applied to the hair using an applicator such as a brush or a sponge. Alternatively, the first and/or the second compositions may be applied to the hair by spraying or foaming the first and/or the second compositions to the hair or by dipping the hair into the first and/or the second composition. Alternatively, the first and/or the second compositions may be applied to the hair using printing technology.

Hair Colouration

The present invention also relates to a hair colouration which is obtainable by the method according to the present invention. As already explained hereinbefore, the structure of the hair colouration is unique in that it is made of alternating polymeric layers which are formed by the alternate deposition of cationic coloured polymers and anionic polymers.

Hair Colouring Kit

The present invention also relates to a hair colouring kit comprising a first compartment comprising the first composition as defined hereinbefore and a second compartment comprising the second composition as defined hereinbefore.

Other Ingredients

The first and/or the second compositions according to the present invention may comprise, in addition to the ingredients indicated above, further ingredients in order to further enhance the properties of the composition, as long as these are not excluded by the claims.

Suitable further ingredients include, but not limited to: oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Oxidizing Agents

The first and/or the second compositions according to the present invention may further comprise at least one source of an oxidizing agent. Any oxidizing agent known in the art may be used. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 liter of deionized water at 25° C. The oxidizing agents are valuable for the initial solubilisation and decolourisation of the melanin (bleaching) and accelerate the oxidation of the oxidative dye precursors (oxidative dyeing) in the hair shaft.

The first and/or the second compositions may comprise a total amount of oxidizing agents ranging from 0.1% to 10%, alternatively from 1% to 7%, alternatively from 2% to 5%, by total weight of the composition.

Suitable water-soluble oxidizing agents include, but are not limited to: inorganic peroxygen materials capable of yielding hydrogen peroxide in an aqueous solution.

Alternatively, the first and/or the second compositions may comprise a total amount of oxidizing agents of less than 1%, alternatively less than 0.5%, alternatively less than 0.3%, alternatively less than 0.1% by total weight of the composition. Alternatively, the first and/or the second compositions may be free of oxidizing agents. By having the first and/or the second compositions which comprise a low amount of oxidizing agents or even no oxidizing agents, these compositions are usually less damaging the hair than standard hair colouring composition which usually comprise a high concentration of oxidizing agent.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

The first and/or the second compositions may comprise a water-soluble oxidizing agent selected from the group consisting of hydrogen peroxide, percarbonates (which may be used to provide a source of both oxidizing agent and carbonate ions and or ammonium ions), persulphates, and mixtures thereof.

When the first and/or the second compositions of the present invention are obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the H2O2 relative to the total weight of the developer composition. A commercial example is the Welloxon® Emulsion with respectively about 6% and about 9% H2O2, marketed by Wella and comprising as INCI ingredients: Water, H2O2, Cetearyl Alcohol, Ceteareth-25, Salicylic Acid, Phosphoric Acid, Disodium Phosphate, Etidronic Acid.

Alkalizing Agents

The first and/or the second compositions according to the present invention may further comprise at least one alkalizing agent. Any alkalizing agent known in the art may be used.

Typically, the first and/or the second compositions may comprise a total amount of alkalizing agents ranging from 0.1% to 10%, alternatively from 0.5% to 6%, alternatively from 1% to 4%, by total weight of the composition.

Alternatively, the first and/or the second compositions may comprise a total amount of alkalizing agents of less than 1%, alternatively less than 0.5%, alternatively less than 0.3%, alternatively less than 0.1% by total weight of the composition. Alternatively, the first and/or the second compositions may be free of alkalizing agents. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The first and/or the second compositions may comprise a total amount of ammonia of less than 1%, alternatively less than 0.5%, alternatively less than 0.3%, alternatively less than 0.1% by total weight of the composition. Alternatively, the first and/or the second compositions may be free of ammonia. These embodiments are particularly interesting in that such compositions are odourless.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The first and/or the second compositions according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the first and/or the second compositions may comprise a total amount of oxidative dye precursors ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6- methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions of the invention are obtained by mixing a tint composition and a developer composition, the primary intermediates and couplers are usually incorporated into the tint composition.

Direct Dyes

The first and/or the second compositions according to the present invention may further comprise compatible direct dyes, in an amount sufficient to provide additional colouring, particularly with regard to intensity. Typically, the first and/or the second compositions may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

The first and/or the second compositions according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first and/or the second compositions may comprise a total amount of chelants ranging from at least 0.01%, alternatively from 0.01% to 5%, alternatively from 0.25% to 3%, alternatively from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety ($-PO_3H_2$) or its derivative $-PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N"-ethylenediamine diacetic acid, their salts thereof, their derivatives thereof, and mixtures thereof.

In a specific embodiment, the composition comprises a chelant selected from the group consisting of diethylenetriamine-N,N',N"-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first and/or the second compositions according to the present invention may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the first and/or the second compositions may comprise a total amount of radical scavengers ranging from 0.1% to 10%, alternatively from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperidine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The first and/or the second compositions according to the present invention may further comprise, in addition to the alkalizing agent discussed above, a pH modifier and/or buffering agent.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The first and/or the second compositions according to the invention may further comprise a thickener in an amount sufficient to provide the compositions with a viscosity so that it can be readily applied to the hair without unduly dripping off the hair and causing mess.

Typically, the first and/or the second compositions may comprise a total amount of thickeners ranging from at least 0.1%, alternatively at least 0.5%, alternatively at least 1%, by total weight of the composition.

Suitable thickeners include, but are not limited to: associative polymers, polysaccharides, non-associative polycarboxylic polymers, and mixtures thereof.

Carbonate Ion Sources

The first and/or the second compositions according to the present invention may further comprise a source of carbonate ions, carbamate ions, hydrogen carbonate ions, and mixtures thereof in a sufficient amount to reduce damage to the hair during the colouring process.

Typically, the first and/or the second compositions may comprise a total amount of a carbonate ion source ranging from 0.1% to 15%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The first and/or the second compositions according to the present invention may further comprise a conditioning agent, and/or be used in combination with a composition comprising a conditioning agent.

Typically, the first and/or the second compositions may comprise a total amount of conditioning agents ranging from 0.05% to 20%, alternatively from 0.1% to 15%, alternatively from 0.2% to 10%, alternatively from 0.2% to 2%, alternatively from 0.5% to 2%, by total weight of the composition.

The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactants

The first and/or the second compositions according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the first and/or the second compositions may comprise a total amount of surfactants ranging from 1% to 60%, alternatively from 2% to 30%, alternatively from 8% to 25%, alternatively from 10% to 20%, by total weight of the composition.

The first and/or the second compositions may comprise a mixture of an anionic surfactant and an amphoteric surfactant with one or more nonionic surfactants. The first and/or the second compositions may comprise a total amount of anionic surfactants ranging from 0.1% to 20%, alternatively from 0.1% to 15%, alternatively from 5% to 15%, by total weight of the compositions; and a total amount of amphoteric and/or nonionic components, which may range independently from each other from 0.1% to 15%, alternatively from 0.5% to 10%, alternatively from 1% to 8%, by total weight of the compositions.

Ionic Strength

The first and/or the second compositions of the present invention may further have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17$ M.

Foam

The first and/or second compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the following section the solvent used to prepare the different compositions is water, unless otherwise specified.

Synthesis Methods for Obtaining the Different Cationic or Anionic Coloured Polymers Used in the Examples Cationic Coloured Polymers
  Polyallylamine hydrochloride labeled with Rhodamine B isothiocyanate (PAH-RhoB iso):
    Starting materials:
      Polyallylamine hydrochloride (PAH), Mw=56,000 Da (CAS: 71550-12-4) available from Sigma-Aldrich
      Rhodamine-B isothiocyanate (RhoB_iso) (CAS: 36877-69-7) available from Sigma-Aldrich
    Synthesis method:
    The following method has been used for labeling Polyallylamine hydrochloride (PAH) with Rhodamine B isothiocyanate (RhoB_iso):
      1) Dissolving 60 mg of Polyallylamine hydrochloride (PAH) in 10 mL of carbonate buffer (pH 9);
      2) Mixing the dissolved polymer with 1 mg of Rhodamine-B isothiocyanate (RhoB_iso) dissolved in 1 mL of DMSO;
      3) Stirring for 24 h at 4° C. and dialyzing against distilled water the resultant mixture.
  Branched polyethyleneimine labeled with Rhodamine B (PEI-RhoB_iso):
    Starting materials:
      Branched polyethyleneimine (PEI), LUPASOL G 500, Mw=25,000 Da (CAS: 9002-98-6) available from BASF
      Rhodamine-B isothiocyanate (RhoB_iso) (CAS: 36877-69-7) available from Sigma-Aldrich
    Synthesis method:
    The same method as for labeling Polyallylamine hydrochloride with Rhodamine B isothiocyanate has been used, wherein PAH was replaced by PEI.

Branched polyethyleneimine labeled with Reactive Red 180 (PEI-Red):
Starting materials:
Branched polyethyleneimine (PEI) (LUPASOL G 500), Mw=25,000 Da, available from BASF (CAS: 9002-98-6)
Reactive Red 180 available from S3 Chemicals (CAS: 72828-03-6).
Synthesis method:
The following method has been used for labeling Branched polyethyleneimine (PEI) with Reactive Red 180 (Red):
1) Dissolving 12.5 g of a 40 wt % solution of Branched polyethyleneimine (PEI) in a 200 ml methanol solution containing 14.05 g of Reactive Red 180;
2) Stirring the suspension at 60° C. for 1 hour;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colorless;
7) Mixing all the resulting supernatant solutions from steps 4) to 6);
8) Adding 12.5 ml of a 32 wt % hydrochloric acid solution to the resulting mixture from step 7)
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and $10^{-4}$ to $10^{-5}$ M HCl
13) Freeze-drying the product Branched polyethyleneimine (PEI) labeled with Remazol brilliant Blue R (PEI-Blue):
Starting materials:
Branched polyethyleneimine (PEI), LUPASOL G 500, Mw=25,000 Da (CAS: 9002-98-6) available from BASF
Remazol brilliant Blue R available from Sigma-Aldrich (CAS: 2580-78-1)
Synthesis method:
The same method as for labeling Branched polyethyleneimine with Reactive Red 180 has been used wherein Reactive Red 180 was replaced by Remazol brilliant Blue R and wherein in step 1) 12.5 g of a 40 wt % Branched polyethyleneimine (PEI) solution were dissolved in a 200 ml methanol solution containing 7.3 g of Remazol brilliant Blue R.

Branched polyethyleneimine labeled with Reactive Blue 116 (PEI-Cyan):
Starting materials:
Branched polyethyleneimine (PEI), LUPASOL G 500, Mw=25,000 Da (CAS: 9002-98-6), available from BASF
Reactive Blue 116 (CAS: 61969-03-7) available from mijn-eigen.nl.
Synthesis method:
The same method as for labeling Branched polyethyleneimine with Reactive Red 180 has been used wherein Reactive Red 180 was replaced by Reactive Blue 116 and wherein in step 1) 12.5 g of a 40 wt % Branched polyethyleneimine (PEI) solution were dissolved in a 200 ml methanol solution containing 11.1 g of Reactive Blue 116.

Polydiallyldimethylammonium chloride copolymerized with Methacryloxyethyl thiocarbamoyl rhodamine B (PDADMAC-RhoB):
Starting materials:
Monomeric diallyldimethylammonium chloride (CAS. 7398-69-8) available from Sigma-Aldrich
Methacryloxyethyl thiocarbamoyl rhodamine B (RhoB), available from Polysciences
Synthesis method:
1.61 g monomeric diallyldimethylammonium chloride and 33 mg methacryloxyethyl thiocarbamoyl rhodamine B were copolymerized in 20 mL 50% methanol at 80° C. under nitrogen atmosphere for 24 hours using 10 mg potassium peroxodisulfate as initiator. After polymerization, the coloured polymer was dialyzed against distilled water.

Anionic Coloured Polymers
Polystyrene sulfonate copolymerized with Rhodamine B isothiocyanate (PSS-RhoB):
Starting materials:
Monomeric Sodium 4-vinylbenzenesulfonate (CAS: 2695-37-6) available from Sigma-Aldrich.
Methacryloxyethyl thiocarbamoyl rhodamine B (RhoB), available from Polysciences
Synthesis method:
The same method as for copolymerizing Polydiallyldimethylammonium chloride with Methacryloxyethyl thiocarbamoyl rhodamine B has been used wherein 1.61 g monomeric diallyldimethylammonium chloride has been replaced by 2.05 g monomeric Sodium 4-vinylbenzenesulfonate.

Cationic Uncoloured Polymer Used in the Following Examples

Branched polyethyleneimine (PEI), LUPASOL G 500, Mw=25,000 Da (CAS: 9002-98-6) available from BASF Anionic Uncoloured Polymers Used in the Following Examples Poly(methacrylic acid) sodium salt (PMAA), Mw=15,000 Da (CAS: 25087-26-7) available from Polysciences, Inc.
Polystyrene sulfonate sodium salt (PSS), Mw=70,000 Da (CAS: 25704-18-1) available from Sigma-Aldrich.
Lambda-Carrageenan (CAS: 9064-57-7) available from Fluka
Dextran sulfate sodium salt, Mw=500,000 Da (CAS: 9011-18-1) available from Fluka.
Sodium alginate (CAS: 9005-38-3) available from Fagron.

The hair swatches which have been used in the following sets of experimental data are natural hair blond hair swatches available from Kerling International Haarfabrik GmbH, Backnang, Germany with the reference number 826533.

First Set of Experimental Data—Examples of Methods According to the Present Invention Wherein Different Types of Anionic Polymers have been Used

Example 1A

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been halved vertically and coloured according to the following protocol:

(i) Preparing the first and second compositions shortly before application;
(ii) Dipping the hair swatch into 5 mL of the first composition at 55° C. in a test tube;
(iii) Agitating the first composition with the hair swatch for 15 min at 55° C. in a laboratory-type drying cabinet;
(iv) Rinsing the hair swatch for 30 s with running lukewarm tap water at a temperature of 30° C. to 35° C.;
(v) Dipping the hair swatch into 5 mL of the second composition at 55° C. in a test tube;
(vi) Agitating the second composition with the hair swatch for 15 min at 55° C. in a laboratory-type drying cabinet;
(vii) Rinsing the hair swatch for 30 s with running lukewarm tap water at a temperature of 30° C. to 35° C.;
(viii) Repeating steps (ii) to (vii) a second time.
(ix) Drying the hair swatch first with tissue paper and then with a hair dryer.

Example 1B

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| Lambda-Carrageenan | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured using the same protocol as for Example 1A.

Example 1C

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| Sodium Alginate | 5.00 (0.5 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured using the same protocol as for Example 1A.

Example 1D

| Ingredients | g/l |
|---|---|
| First Composition | |
| PEI-Red | 5.00 (0.5 wt %) |
| NaCl | 11.69 (0.2 mol/l) |
| Triethanolamine | 7.46 (0.05 mol/l) |
| pH adjusted to: 8 by adding 1.0 mol/l NaOH or 1.0 mol/l HCl | |
| Second Composition | |
| Dextran sulfate Sodium salt | 5.00 (0.5 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured using the same protocol as for Example 1A.

Conclusion:

Examples 1A to 1D demonstrates that a high diversity of anionic polymer may be used in the method according to the present invention.

Second Set of Experimental Data—Comparison Between the Method According to the Present Invention and a Method for Colouring Hair Using Direct Dyes

Example 2A

| Ingredients | g/l |
|---|---|
| First Composition | |
| PAH-RhoB_iso | 1.00 (0.1 wt %) |
| NaCl | 11.69 (0.2 mol/L) |
| Sodium acetate | 3.71 |
| Acetic acid | 0.85 |

-continued

| | |
|---|---|
| pH adjusted to 5.6 by adding 1.0 mol/l NaOH or 1.0 mol/l HCl |
| Second Composition | |
| PSS | 1.00 (0.1 wt %) |
| NaCl | 11.69 (0.2 mol/L) |
| Sodium acetate | 3.71 |
| Acetic acid | 0.85 |
| pH adjusted to 5.6 by adding 1.0 mol/l NaOH or 1.0 mol/l HCl |

A hair swatch has been coloured according to the following protocol:
(i) Preparing the first and second compositions shortly before application;
(ii) Dipping the hair swatch into 10 mL of the first composition at 40° C. in a test tube;
(iii) Agitating the first composition with the hair swatch for 30 min at 40° C. in a laboratory-type drying cabinet;
(iv) Rinsing the hair swatch three times with fresh 10 ml lukewarm tap water at a temperature of 30° C. to 35° C. in a test tube while stirring for 5 min;
(v) Dipping the hair swatch into 10 mL of the second composition at 40° C. in a test tube;
(vi) Agitating the second composition with the hair swatch for 30 min at 40° laboratory-type drying cabinet;
(vii) Rinsing the hair swatch three times with fresh 10 ml lukewarm tap water at a temperature of 30° C. to 35° C. in a test tube while stirring for 5 min;
(viii) Repeating steps (ii) to (vii) a second time.
(ix) Drying the hair swatch first with tissue paper and then with a hair dryer Example 2B

| Ingredients | g/l |
|---|---|
| First Composition | |
| PDADMAC-RhoB | 1.00 (0.1 wt %) |
| NaCl | 11.69 (0.2 mol/L) |
| Sodium acetate | 3.71 |
| Acetic acid | 0.85 |
| pH adjusted to 5.6 by adding 1.0 mol/l NaOH or 1.0 mol/l HCl |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl |

A hair swatch has been coloured following the same experimental protocol as in Example 2A.

Example 2C

| Ingredients | g/l |
|---|---|
| First Composition | |
| PEI-RhoB_iso | 1.00 (0.1 wt %) |
| NaCl | 11.69 (0.2 mol/l) |
| Sodium acetate | 3.71 |
| Acetic acid | 0.85 |

-continued

| Ingredients | g/l |
|---|---|
| pH adjusted to 5.6 by adding 1.0 mol/l NaOH or 1.0 mol/l HCl |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl |

A hair swatch has been coloured following the same experimental protocol as in Example 2A.

Example 2D

| Ingredients | g/l |
|---|---|
| First Composition | |
| PAH-RhoB_iso | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl |
| Second Composition | |
| PMAA | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl |

A hair swatch has been coloured following the same experimental protocol as in Example 2A.

Example 2E

| Ingredients | g/l |
|---|---|
| First Composition | |
| PDADMAC-RhoB | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl |
| Second Composition | |
| PMAA | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl |

A hair swatch has been coloured following the same experimental protocol as in Example 2A.

Comparative Example 1

| Direct Dye composition | |
|---|---|
| Ingredients | g/l |
| Rhodamine B[1] | 0.25 (0.025 wt %) |
| | pH: 7 |

[1]Rhodamine B (CAS: 81-88-9) available from Fluka

A hair swatch has been coloured according to the following experimental protocol:

(i) Preparing the direct dye composition;
(ii) Dipping the hair swatch into 10 mL of the direct dye composition at 40° C. in a test tube;
(iii) Agitating the direct dye composition with the hair swatch for 30 min at 40° C. in a laboratory-type drying cabinet;
(iv) Rinsing the hair swatch three times with fresh 10 ml lukewarm tap water at a temperature of 30° C. to 35° C. in a test tube while stirring for 5 min;
(v) Repeating steps (ii) to (iv) a second time;
(vi) Drying the hair swatch first with tissue paper and then with a hair dryer.

Washing with Shampoo:

Each of the coloured hair swatches which have been obtained in examples 2A to 2E and in comparative example 1 were washed 5 times with a neutral shampoo using the following procedure:

(i) Wetting the hair swatch with running tap water for 10 s;
(ii) Adding 2-3 drops of a shampoo to the hair swatch;
(iii) Rubbing the hair swatch with fingers for 30 s;
(iv) Rinsing the hair swatch with running tap water at a temperature of 30° C. to 35° C.;
(v) Repeating steps (ii) to (iv) four more times
(vi) Drying the hair swatch first with tissue paper and then with a hair dryer.

Colour Intensity:

Measurement

The colour intensity of the coloured hair swatches obtained in example 2A to 2E has been compared visually with the colour intensity of the coloured hair swatch obtained in comparative example 1.

Result and Conclusion

The colour intensity of the coloured hair swatches obtained in examples 2A to 2E was higher than the colour intensity of the coloured hair swatch of comparative example 1. Hence, colouring the hair according to the method of the present invention provides a better colour intensity than colouring the hair with a direct dye composition.

Washfastness:

Measurement

The washfastness of each of the coloured hair swatches obtained in examples 2A to 2E and in comparative example 1 has been evaluated visually comparing the colour intensity of the hair swatch before and after washing the hair swatch with shampoo according to the above procedure.

Result and Conclusion

The coloured hair swatches obtained in examples 2A to 2E have a better washfastness than the coloured hair swatch obtained in comparative example 1.

Third Set of Experimental Data—Influence of the pH of the First and Second Compositions which are Used in the Method According to the Present Invention on the Colour Intensity of the Hair Colouration

Example 3A

| Ingredients | g/l |
|---|---|
| First Composition | |
| PEI-Blue | 2.00 (0.2 wt %) |
| NaCl | 11.69 (0.2 mol/l) |
| Sodium acetate | 3.71 |
| Acetic acid | 0.85 |
| pH adjusted to 5 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been halved vertically and coloured according to the following protocol:

(i) Preparing the first and second compositions shortly before application;
(ii) Dipping the hair swatch into 5 mL of the first composition at 45° C. in a test tube;
(iii) Agitating the first composition with the hair swatch for 20 min at 45° C. in a laboratory-type drying cabinet;
(iv) Rinsing the hair swatch for 30 s with running lukewarm tap water at a temperature of 30° C. to 35° C.;
(v) Dipping the hair swatch into 5 mL of the second composition at 45° C. in a test tube;
(vi) Agitating the second composition with the hair swatch for 20 min at 45° C. in a laboratory-type drying cabinet;
(vii) Rinsing the hair swatch for 30 s with running lukewarm tap water at a temperature of 30° C. to 35° C.;
(viii) Repeating steps (ii) to (vii) a second time.
(ix) Drying the hair swatch first with tissue paper and then with a hair dryer

Example 3B

| Ingredients | g/l |
|---|---|
| First Composition | |
| PEI-Blue | 2.00 (0.2 wt %) |
| NaCl | 11.69 (0.2 mol/l) |
| Sodium acetate | 3.71 |
| Acetic acid | 0.85 |

| Ingredients | g/l |
|---|---|
| pH adjusted to 6 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental proctocol as in Example 3A.

Example 3C

| Ingredients | g/l |
|---|---|
| First Composition | |
| PEI-Blue | 2.00 (0.2 wt %) |
| NaCl | 11.69 (0.2 mol/l) |
| HEPES(4-(2-hydroxyethyl)-1-piperazineethanesulfonic acid) | 11.92 (0.05 mol/l) |
| pH adjusted to 7 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

A hair swatch has been coloured following the same experimental proctocol as in Example 3A.

Example 3D

| Ingredients | g/l |
|---|---|
| First Composition | |
| PEI-Blue | 2.00 (0.2 wt %) |
| NaCl | 11.69 (0.2 mol/l) |
| HEPES(4-(2-hydroxyethyl)-1-piperazineethanesulfonic acid) | 11.92 (0.05 mol/l) |
| pH adjusted to 8 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured following the same experimental proctocol as in Example 3A.

Example 3E

| Ingredients | g/l |
|---|---|
| First Composition | |
| PEI-Blue | 2.00 (0.2 wt %) |
| NaCl | 11.69 (0.2 mol/l) |
| Ethanolamine | 3.05 (0.05 mol/l) |
| pH adjusted to: 9 by adding 1.0 mol/l NaOH or 1.0 mol/l HCl | |
| Second Composition | |
| PSS | 2.00 (0.2 wt %) |
| NaCl | 11.69 (0.2 mol/l) |
| Sodium acetate | 3.71 |
| Acetic acid | 0.85 |
| pH adjusted to: 5.6 by adding 1.0 mol/l NaOH or 1.0 mol/l HCl | |

A hair swatch has been coloured following the same experimental proctocol as in Example 3A.

Colour Intensity:

Measurement

The colour intensity of each of the coloured hair swatches obtained in example 3A to 3E has been compared visually.

Result and Conclusion

The colour intensity increases proportionally to the pH of the first composition. Nevertheless, one of the advantages of the method according to the present invention is that the hair may be coloured with a good colour intensity even if the compositions which are used have a lower pH than standard oxidative hair colouring compositions. Using compositions with a lower pH than standard oxidative hair colouring compositions may reduce the risk of damaging the hair.

Fourth Set of Experimental Data—Influence of the Number of Sequences of Steps and of the Type of Outermost Layer on Colour Intensity and Washfastness of the Hair Colouration In the following set of data, the following first and second compositions have been used. The first and second compositions have been prepared shortly before application.

| Ingredients | g/l |
|---|---|
| First Composition | |
| PEI-Red | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |
| Second Composition | |
| PSS | 1.00 (0.1 wt %) |
| NaCl | 11.69 (0.2 mol/l) |
| Sodium acetate | 3.71 |
| Acetic acid | 0.85 |
| pH adjusted to 5.6 by adding 1.0 mol/l NaOH or 1.0 mol/l HCl | |

Examples 4A to 4G

In each of the following examples, the first and the second compositions have been applied to a hair swatch according to different sequences, alternating the application of the first composition with the application of the second composition. The first and the second compositions have been prepared shortly before application.

The first composition has been applied to the hair according to the following protocol:
 (i) Dipping the hair swatch into 5 mL of the first composition at 55° C. in a test tube;
 (ii) Agitating the first composition with the hair swatch for 15 min at 55° C. in a laboratory-type drying cabinet;
 (iii) Rinsing the hair swatch with lukewarm tap water at a temperature of 30° C. to 35° C.

The second composition has been applied to the hair according to the following protocol:
 (i) Dipping the hair swatch into 5 mL of the second composition at 55° C. in a test tube;
 (ii) Agitating the second composition with the hair swatch for 15 min at 55° C. in a laboratory-type drying cabinet;
 (iii) Rinsing the hair swatch with lukewarm tap water at a temperature of 30° C. to 35° C.;

At the end of each of the sequence of application of the first and the second compositions to the hair, the hair swatch has been dried first with tissue paper and then with a hair dryer Sequences of Application of the First and the Second Compositions to the Hair:

| Example | Sequence |
| --- | --- |
| Example 4A | PEI-Red/PSS |
| Example 4B | PEI-Red/PSS/PEI-Red |
| Example 4C | (PEI-Red/PSS)2 |
| Example 4D | (PEI-Red/PSS)2/PEI-Red |
| Example 4E | (PEI-Red/PSS)3 |

-continued

| Example | Sequence |
| --- | --- |
| Example 4F | (PEI-Red/PSS)3/PEI-Red |
| Example 4G | (PEI-Red/PSS)4 |

Comparative Example 2

A hair swatch has been coloured according to the following protocol:
 (i) Dipping the hair swatch into 5 mL of the first composition at 55° C. in a test tube;
 (ii) Agitating the first composition with the hair swatch for 15 min at 55° C. in a laboratory-type drying cabinet;
 (iii) Rinsing the hair swatch with lukewarm tap water at a temperature of 30° C. to 35° C.

Washing with Shampoo:

Each of the coloured hair swatches which have been obtained in examples 4A to 4G and in comparative example 2 were washed 3 times with Wella Brillance Shampoo available in Germany in August 2014 using the following procedure:
 (i) Wetting the hair swatch with running tap water for 10 s;
 (ii) Adding 2-3 drops of a shampoo to the hair swatch;
 (iii) Rubbing the hair swatch with fingers for 30 s;
 (iv) Rinsing the hair swatch with running tap water at a temperature of 30° C. to 35° C.;
 (v) Repeating steps (ii) to (iv) two more times;
 (vi) Drying the hair swatch first with tissue paper and then with a hair dryer.

L*, a*, b* Measurements

The colorimetric parameters in the CIE L* a* b* system are measured for each of the hair swatches obtained in Example 4A to 4G and in comparative example 2 before and after washing using a Minolta CM-508i spectrophotometer (illuminant is D65 daylight with 10° observer) in which L* represents the lightness of the colour, a* indicates the green/red colour axis and b* the blue/yellow colour axis.

Overall color change is represented by ΔE where ΔE is defined by the following formula:

$$\Delta E=[(\Delta L^*)^2+(\Delta a^*)^2+(\Delta b^*)^2]^{1/2}$$

Results and Conclusion:

| Example | Type of layers | Before washing L* | a* | b* | After three times washing with shampoo L* | a* | b* | ΔE |
| --- | --- | --- | --- | --- | --- | --- | --- | --- |
| Comparative Example 2 | PEI-Red | −19.31 | 30.94 | −7.62 | −13.90 | 27.50 | −8.46 | 6.47 |
| Example 4A | PEI-Red/PSS | −18.62 | 30.75 | −8.51 | −15.65 | 27.93 | −8.09 | 4.12 |
| Example 4B | PEI-Red/PSS/PEI-Red | −23.71 | 30.29 | −7.33 | −19.46 | 30.23 | −8.62 | 4.44 |
| Example 4C | (PEI-Red/PSS)2 | −24.93 | 32.32 | −7.03 | −22.37 | 30.74 | −7.88 | 3.13 |
| Example 4D | (PEI-Red/PSS)2/PEI-Red | −27.21 | 26.43 | −6.09 | −25.08 | 27.35 | −6.90 | 2.46 |
| Example 4E | (PEI-Red/PSS)3 | −27.87 | 28.24 | −6.62 | −26.03 | 27.74 | −7.00 | 1.94 |
| Example 4F | (PEI-Red/PSS)3/PEI-Red | −28.66 | 24.86 | −6.00 | −26.73 | 24.88 | −6.79 | 2.09 |
| Example 4G | (PEI-Red/PSS)4 | −29.34 | 25.08 | −6.72 | −27.35 | 24.04 | −6.96 | 2.26 |

When comparing the L* values measured for examples 4A, 4C, 4E and 4G before washing, it can be noticed that the colour intensity of hair coloured with the first and second compositions according to the present invention increases with increased number of times the sequence of steps of the method according to the present invention is repeated.

When comparing the ΔE values measured for examples 4A, 4C and 4E, it can be noticed that the ΔE value decreases with increased number of times the sequence of steps of the method according to the present invention is repeated.

When comparing the ΔE values obtained for example 4A vs. comparative example 2 or for example 4C vs. example 4B or for example 4E vs. example 4D, the ΔE value is usually lower when the last layer which is positioned on top of the hair is made of an anionic polymer, i.e. the hair colouration obtained on hair is characterized by a better washfastness. This demonstrates that the anionic layer may act as a protective layer for the cationic coloured layer which is placed underneath.

Fifth Set of Experimental Data—Examples of a Method According to the Present Invention Wherein a First Composition Comprising a Cationic Coloured Polymer and a Second Composition Comprising an Anionic Coloured Polymer have been Used Example 5

| Ingredients | g/l |
|---|---|
| First Composition | |
| PEI-Cyan | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS-RhoB | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the following protocol:
(i) Preparing the first and second compositions shortly before application;
(ii) Dipping the hair swatch into 5 mL of the first composition at 55° C. in a test tube;
(iii) Agitating the first composition with the hair swatch for 15 min at 55° C. in a laboratory-type drying cabinet;
(iv) Rinsing the hair swatch with lukewarm tap water at a temperature of 30° C. to 35° C.;
(v) Dipping the hair swatch into 5 mL of the second composition at 55° C. in a test tube;
(vi) Agitating the second composition with the hair swatch for 15 min at 55° C. in a laboratory-type drying cabinet;
(vii) Rinsing the hair swatch with lukewarm tap water at a temperature of 30° C. to 35° C.

Comparative Example 3

| Ingredients | g/l |
|---|---|
| First Composition | |
| PEI-Cyan | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the same protocol as for Example 5 using the above first and second compositions.

Comparative Example 4

| Ingredients | g/l |
|---|---|
| First Composition | |
| PEI | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |
| Second Composition | |
| PSS-RhoB | 5.00 (0.5 wt %) |
| NaCl | 11.69 (0.2 mol/l) |
| Triethanolamine | 7.46 (0.05 mol/l) |
| pH adjusted to 8 by adding 1.0 mol/l NaOH or 1.0 mol/l HCl | |

A hair swatch has been coloured according to the same protocol as for Example 5 using the above first and second compositions.

L*, a*, b* Measurements

The colorimetric parameters in the CIE L* a* b* system have been measured for each of the hair swatches obtained in example 5 and in comparative examples 3 and 4 before and after colouring using a Minolta CM-508i spectrophotometer (illuminant is D65 daylight with 10° observer) in which L* represents the lightness of the colour, a* indicates the green/red colour axis and b* the blue/yellow colour axis.

Results and Conclusion:

| Example | Layers | Before colouring | | | | After colouring | | | |
|---|---|---|---|---|---|---|---|---|---|
| | | L* | a* | b* | Colour | L* | a* | b* | Colour |
| Comparative example 3 | PEI-Cyan/PSS | 14.08 | 1.81 | 7.05 | Blond | 2.22 | −13.63 | −1.73 | Cyan |
| Comparative example 4 | PEI/PSS-Rho | 13.42 | 1.74 | 7.28 | Blond | −2.57 | 19.81 | −6.76 | Red |
| Example 5 | PEI-Cyan/PSS-Rho | 12.75 | 1.94 | 7.76 | Blond | −10.37 | 6.47 | −14.71 | Purple |

As can be seen in this set of experimental data, the first composition used in example 5 comprises a cationic coloured polymer and the second composition used in example 5 comprises an anionic coloured polymer. When both coloured first and second composition have been applied onto hair, the resultant colour which was obtained was different from the colour which was obtained when either the first coloured composition or the second coloured composition have been applied onto hair. Therefore, it is possible to combine different cationic and anionic coloured polymers in order to obtain in an easy manner the desired colour result.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for colouring hair comprising:
    a) carrying out the following sequence of steps:
        i) applying a first composition comprising colored cationic polymer to a first portion of the hair, wherein the colored cationic polymer is polyethleneimine; and
        ii) applying a second composition comprising anionic polymer to a second portion of the hair, wherein the anionic polymer is a dextran sulfate sodium salt;
        the first and the second portions of the hair having at least one common area; and the first composition comprises a total concentration of polyethleneimine ranging from 0.1 g/L to 100 g/L or the second composition comprises a total concentration of dextran sulfate sodium salt ranging from 0.1 g/L to 100 g/L.

2. The method according to claim 1, wherein the method further comprises:
    b) repeating step a) at least once, wherein the common area of each of the repeated steps a) has at least one common area with:
        the common area of step a); and
        the common area of each of the other repeated steps a) in case step a) is repeated more than once.

3. The method according to claim 1, wherein step i) or ii) further comprises the subsequent sub-steps of:
    removing the excess of respectively the first composition or the second composition from the hair or
    applying energy to the hair in the form of heat, ultrasounds, infrared or microwaves or washing or rinsing the hair.

4. The method according to claim 1, wherein:
    the colored cationic polymer has a weight average molecular weight ranging from 0.5 kD to 5000 kD and
    the anionic polymer has a weight average molecular weight ranging from 10 kD to 1000 kD.

5. The method according to claim 1, wherein the first or the second composition has a pH ranging from 2 to 14.

6. The method according to claim 1, wherein the first or the second composition comprises a cosmetically acceptable salt at a concentration ranging from 0.05 to 1.5 mat.

7. The method according to claim 1, wherein prior to step a), the hair is pretreated to modify the number of positive or negative charges in some portions of the hair or all over the hair.

* * * * *